US012396967B2

(12) United States Patent
Sekhavat et al.

(10) Patent No.: US 12,396,967 B2
(45) Date of Patent: *Aug. 26, 2025

(54) METHOD OF TREATING A PERSON AFFLICTED WITH A RESPIRATORY CONDITION AND PHARMACEUTICAL FORMULATION INCLUDING DAPSONE

(71) Applicant: Pulmonem Inc., Dieppe (CA)

(72) Inventors: Houfar Sekhavat, Dieppe (CA); Satish Asotra, Brampton (CA)

(73) Assignee: PULMONEM INC., Dieppe (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/520,091

(22) Filed: Nov. 27, 2023

(65) Prior Publication Data

US 2024/0091178 A1  Mar. 21, 2024

Related U.S. Application Data

(63) Continuation of application No. 17/955,337, filed on Sep. 28, 2022, now Pat. No. 11,826,323, which is a continuation-in-part of application No. PCT/CA2021/050425, filed on Mar. 30, 2021.

(60) Provisional application No. 63/029,685, filed on May 25, 2020, provisional application No. 63/001,972, filed on Mar. 30, 2020.

(51) Int. Cl.
| | |
|---|---|
| *A61K 31/145* | (2006.01) |
| *A61K 9/00* | (2006.01) |
| *A61K 9/06* | (2006.01) |
| *A61K 9/14* | (2006.01) |
| *A61K 31/10* | (2006.01) |
| *A61K 31/65* | (2006.01) |
| *A61K 31/7052* | (2006.01) |
| *A61K 47/14* | (2017.01) |
| *A61K 47/42* | (2017.01) |
| *A61K 47/44* | (2017.01) |
| *A61M 15/00* | (2006.01) |
| *A61P 11/00* | (2006.01) |

(52) U.S. Cl.
CPC .......... *A61K 31/145* (2013.01); *A61K 9/0043* (2013.01); *A61K 9/0075* (2013.01); *A61K 9/06* (2013.01); *A61K 9/14* (2013.01); *A61K 31/10* (2013.01); *A61K 31/65* (2013.01); *A61K 31/7052* (2013.01); *A61K 47/14* (2013.01); *A61K 47/42* (2013.01); *A61K 47/44* (2013.01); *A61M 15/0028* (2013.01); *A61M 15/0065* (2013.01); *A61P 11/00* (2018.01); *A61M 2202/064* (2013.01)

(58) Field of Classification Search
CPC ...... A61K 31/10; A61K 31/145; A61K 31/65; A61K 31/7052; A61K 47/14; A61K 47/42; A61K 47/44; A61K 9/0019; A61K 9/0043; A61K 9/0046; A61K 9/0075; A61K 9/0095; A61K 9/02; A61K 9/06; A61K 9/14; A61K 9/7038; A61P 11/00
See application file for complete search history.

(56) References Cited

U.S. PATENT DOCUMENTS

| | | | |
|---|---|---|---|
| 5,207,217 A | 5/1993 | Cocozza et al. | |
| 7,531,694 B2 | 5/2009 | Villa et al. | |
| 9,845,289 B2 | 12/2017 | Baratella et al. | |
| 10,285,945 B2 | 5/2019 | Johnston et al. | |
| 2003/0232019 A1 | 12/2003 | Basu | |
| 2009/0111780 A1 | 4/2009 | Giordano | |
| 2013/0251790 A1 | 9/2013 | Malhotra | |
| 2015/0040894 A1 | 2/2015 | Rubin | |
| 2020/0338023 A1 * | 10/2020 | Pisak | A61K 47/44 |

FOREIGN PATENT DOCUMENTS

| | | | | |
|---|---|---|---|---|
| KR | 20200124185 A | 11/2020 | | |
| WO | WO2003061767 A1 * | 7/2003 | | |
| WO | WO-2005041864 A2 * | 5/2005 | .......... | A61K 31/415 |
| WO | WO-2011115778 A2 * | 9/2011 | ............ | A61K 31/10 |
| WO | 2022039286 A1 | 2/2022 | | |

OTHER PUBLICATIONS

Kast, Experimental Lung Research, 2020, p. 1-5 (Year: 2020).*
Gujski (Viruses 2022, 14, 76. https://doi.org/10.3390/v14010076) (Year: 2022).*
Juanes-Velasco et al, (Frontiers in Immunology, Jan. 2022 | vol. 13). (Year: 2022).*
Gong Jing et al, "Correlation Analysis Between Disease Severity and Inflammation-related Parameters in Patients with COVID-19 Pneumonia", medRxiv, doi: 10.1101/2020.02.25.20025643 Feb. 27, 2020.
Kanoh Soichiro et al, "Dapsone inhibits IL-8 secretion from human bronchial epithelial cells stimulated with lipopolysaccharide and resolves airway inflammation in the ferret", Chestunited States Feb. 9, 2018, Elsevier Inc, United States, vol. 140, No. 4, doi: 10.1378/CHEST.10-2908, ISSN 1931-3543 Dec. 16, 2015.
Ali Ahmed S et al, "Pharmacological basis for the potential role of Azithromycin and Doxycycline in management of COVID-19", Arabian Journal of Chemistry, Elsevier, Amsterdam, NL, vol. 14, No. 3, doi: 10.1016/J.ARABJC.2020.102983, ISSN 1878-5352 Jan. 10, 2021.
Report of the WHO-China Joint Mission on Coronavirus Disease 2019 (COVID-19), Feb. 16-24, 2020, pp. 1-40.
World Health Organization Model List of Essential Medicines, 21st List, 2019.

(Continued)

*Primary Examiner* — Umamaheswari Ramachandran
(74) *Attorney, Agent, or Firm* — Smart & Biggar LP

(57) ABSTRACT

A method for treating patients with COVID-19 and/or other respiratory conditions includes administering eighty-five milligrams of dapsone twice daily for twenty-one days. A variety of dapsone formulations and delivery devices are disclosed, including an inhaler, nasal spray, nasal gel, otic formulation, intravenous formulation, oral solution, oral suspension, patch and suppository.

16 Claims, No Drawings

(56) References Cited

OTHER PUBLICATIONS

White, P. Lewis et al., "Therapy and Management of Pneumocystis jirovecii Infection," Journal of Fungi, Nov. 22, 2018, Basel, Switzerland.

Sangiolo, Dario et al., "Toxicity and Efficacy of Daily Dapsone as Pneumocystis jiroveci Prophylaxis after Hematopoietic Stem Cell Transplantation: A Case-Control Study," Biology of Blood and Marrow Transplantation, I I: 521-529 (2005).

Hughes, Walter T., "Use of Dapsone in the Prevention and Treatment of Pneumocystis carinii Pneumonia: A Review," Clinical Infectious Diseases, 1998:27: 191-204.

"Guidelines for the Prevention and Treatment of Opportunistic Infections in Adults and Adolescents with HIV," 2. https://clinicalinfo.hiv.gov/en/guidelines/adult-and-adolescent-opportunistic-infection/table-1-prophylaxis-prevent-first-episode, Oct. 13, 2021.

Wu, Shi Xiu et al., "A clinical study of six causes of pneumocystis carinii pneumonia," Zhongua Jie He He Hu Xi Za Zhi, Chinese Journal of Tuberculosis and Respiratory Diseases, 21(10), pp. 590-592, Oct. 1998.

Kanwar, Badar, et al., "Specific Treatment Exists for SARS-CoV-2 ARDS," Vaccines, 2021, 9, 635, https://doi.org/10.3390/vaccines9060635.

Willis et al., "Therapeutic Liposomal Dry Powder Inhalation Aerosols for Targeted Lung Delivery," Lung, 190(3), pp. 251-262, Jan. 25, 2012, available at https://doi.org/10.1007/s00408-011-9360-x.

International Search Report and Written Opinion for PCT/CA2021/050425 dated Jun. 15, 2021.

Saillour-Glenisson et al., Effect of dapsone on survival in HIV infected patients: a meta-analysis of finished trials., Rev Epidemiol Sante Publique, 2000 Han; 48(1): 17-30.

Corallo, Carmela Emma, Coutsouvelis, John, Morgan, Susan, Morrissey, Orla and Avery, Sharon. "Dapsone for Pneumocystis jirovecii pneumonia prophylaxis—applying theory to clinical practice with a focus on drug interactions" Drug Metabolism and Personalized Therapy, vol. 35, No. 3, 2020, pp. 20190018.

Australian Medicines Handbook, pp. 157-158 and 210.

Kanwar et al., "Benefits of Using Dapsone in Patients Hospitalized with COVID-19," Vaccines, 2022, 10, 195, https://doi.org/10.3390/vaccines10020195.

Veiga, Viviane C., "Effect of tocilizumab on clinical outcomes at 15 days in patients with severe or critical coronavirus disease 2019: randomised controlled trial," BMJ, 2021: 372:n84, https://www.bmj.com/content/372/bmj.n84.

"Use of systemic corticosteroids linked with worse COVID-19 outcomes," https://www.healio.com/news/pulmonology/20210927/use-of-systemic-corticosteroids-linked-with-worse-covid19-outcomes, Sep. 27, 2021.

Galimberti, Fabrizio, et al., Evidence-based best practice advice for patients treated with systemic immunosuppressants in relation to COVID-19, Clinics in Dermatology (2020), 38, 775-780.

Boulware, David R., et al., "A Randomized Trial of Hydroxychloroquine as Postexposure Prophylaxis for Covid-19," N Engl J Med., Aug. 6, 2020, 383(6): 517-525.

Bull-Otterson, Lara et al., "Hydroxychloroquine and Chloroquine Prescribing Patterns by Provider Specialty Following Initial Reports of Potential Benefit for COVID-19 Treatment," https://www.cdc.gov/mmwr/volumes/69/wr/mm6935a4.htm, Jan.-Jun. 2020, MMWR.

Farouk et al. (Medical Hypothesis, Apr. 21, 2020), (Year: 2020).

Altschuler et al. (Medical Hypothesis, Apr. 21, 2020) (Year: 2020).

Chougule et al. (AAPS PharmSciTech, 9, Mar. 1, 2008). (Year: 2008).

Zhang et al. (Clinical Immunology, 2020, Mar. 25, 2020). (Year: 2020).

Gautret et al. (Int J of Antimicrobial Agents, 56, 2020, p. 1-6). (Year: 2020).

Extended European Search Report re: EP Application No. 21742678.2 Sep. 9, 2022.

Office Action for U.S. Appl. No. 17/386,263 dated Dec. 16, 2021.

Office Action for U.S. Appl. No. 17/955,337 dated Mar. 9, 2023.

\* cited by examiner

METHOD OF TREATING A PERSON AFFLICTED WITH A RESPIRATORY CONDITION AND PHARMACEUTICAL FORMULATION INCLUDING DAPSONE

CROSS REFERENCE TO RELATED APPLICATIONS

This application is a continuation of U.S. application Ser. No. 17/955,337, filed Sep. 28, 2022, which is a continuation-in-part of International Application No. PCT/CA2021/050425, filed Mar. 30, 2021, which claims priority to U.S. Provisional Patent Application No. 63/001,972, filed Mar. 30, 2020, and U.S. Provisional Patent Application No. 63/029,685, filed May 25, 2020. The contents of all of said applications are incorporated herein by reference.

TECHNICAL FIELD

The present invention relates to the medical field. An embodiment of the invention comprises a method for treating a person afflicted with a respiratory condition, and another embodiment of the invention comprises a pharmaceutical formulation.

BACKGROUND

The Coronavirus disease 2019 (COVID-19) pandemic is a public health emergency. It has focused worldwide attention and efforts towards rapid identification and implementation of mitigation strategies at an unprecedented rate. This disease threatens to overwhelm existing healthcare capacities of countries despite their maximal emergency preparedness. No approved drugs specifically for anti-inflammatory treatment of patients with COVID-19 currently exist.

As of Apr. 7, 2020, the World Health Organization (WHO) reported 1,279,722 confirmed cases and 72,614 deaths globally. COVID-19 is caused by the severe acute respiratory syndrome coronavirus 2 (SARS-CoV-2), which unlike previous coronavirus outbreaks, such as the severe acute respiratory syndrome (SARS) and Middle East respiratory syndrome (MERS) outbreaks, has spread rapidly and has been reported from 183 countries and territories around the world, including the United States and Canada. The case fatality is of great concern with estimates suggesting that SARS-CoV-2 may be more lethal than seasonal influenza (estimated mortality rate of 0.5-5% (Report of the WHO-China Joint Mission on Coronavirus Disease 2019 (COVID-19), 2020) (Wilson et al., 2020)). In the United States, the overall cumulative hospitalization rate was 12.3 per 100,000 population, with the highest rates in those aged 65 years and older (38.7 per 100,000) followed by adults aged 50-64 years (20.7 per 100,000) (COVID View Weekly Summary|CDC, 2020).

Data from China suggests an overall case fatality rate (CFR) of 2.3% (Z. Wu & McGoogan, 2020). Reported CFRs vary from country to country (for example, 1% in Germany to 11% in Italy). The study reports variations by age (China: 8.0% for 70-79 years old; 14.8% for >80 years of age) and comorbidity (China: 10.5% with cardiovascular disease; 7.3% with diabetes; 6.3% with chronic respiratory disease; and 6.0% with hypertension) (COVID View Weekly Summary|CDC, 2020). This could be indicative of underlying demographic variability, including population burden of comorbidity, which can affect respective CFRs from countries affected. Among those developing COVID-19, 14% of the patients have been severely affected (i.e., dyspnea, respiratory frequency 30/min, blood oxygen saturation 93%, partial pressure of arterial oxygen to fraction of inspired oxygen ratio <300, and/or lung infiltrates >50% within 24 to 48 hours), and 5% were critically affected (i.e., respiratory failure, septic shock, and/or multiple organ dysfunction or failure) (COVID View Weekly Summary|CDC, 2020). Death has been largely reported due to massive alveolar damage and progressive respiratory failure (Chan et al., 2020) (C. Huang et al., 2020). Those experiencing severe COVID-19 often require hospitalization with support ranging from supplemental oxygen to mechanical ventilation. While healthcare systems in developed countries are well-equipped to provide necessary care, a sudden unprecedented demand could severely strain even these systems' resources, with the real possibility of being overpowered if efforts fail to moderate the rate of growth of COVID-19 cases requiring hospitalization. This also impacts the continuity of care for all (including non-COVID) patients, especially those living with chronic conditions.

In the United States, as of Apr. 14, 2020, a total of 579,005 COVID-19 cases have been reported from 55 jurisdictions (Coronavirus (COVID-19) cases by day U.S. 2020|Statista, 2020) and 29,300 new cases were reported on Apr. 14, 2020 alone. Data from Apr. 4, 2020 shows a rise in the hospitalization rate to 12.2 per 100,000 population from 7.2 per 100,000 population in the preceding week. The mortality rate in the corresponding weeks attributed to COVID-19 mirrored the rise, at 6.9% during the week of April 4, from 4.0% during the preceding week (COVID View Weekly Summary|CDC, 2020). The per 100,000 hospitalization rates rise steadily with age among those above 50 years [20.7 (50-64 years), 31.2 (65-74 years), 45.6 (75-84 years) and 59.1 (85+ years)]. Data from New York City on April 8th show the highest COVID-19 death rate of 356.87 per 100,000 population among those aged 75 years and older, against a city-wide rate of 50.72 per 100,000 population and 152.19 per 100,000 population in the 65-74 years age group (COVID-19 death rates by age group in New York City 2020|Statista, 2020).

As of Apr. 13, 2020, data from Québec reveals that we have 13,557 confirmed cases, 879 hospitalizations (including 226 in intensive care) and 360 deaths (CFR 2.65%) with the majority of deaths in the eighty and above age groups (Situation of the coronavirus (COVID-19) in Québec|Gouvernement du Québec, 2020). As of Apr. 13, 2020, in Canada, 24,835 cases have been confirmed, 557 ICU admissions and 735 deaths (CFR 2.9%) (Epidemiological summary of COVID-19 cases in Canada—Canada.ca, 2020). In the USA where the testing has been more limited and heterogeneous, 579,005 cases have been reported, with 22,252 deaths (CFR 3.8%) (Cases in U.S.|CDC, 2020). According to the Centers for Disease Control (CDC). According to the Centers for Disease Control (CDC), the majority of patients hospitalized have some type of comorbidity including Hypertension, Cardiovascular diseases, Obesity, Chronic respiratory disease or Diabetes (Situation Summary|CDC, 2020).

With expanding testing capacity, there is a growing ability to identify COVID-19 cases at its pre-hospitalization stages. With the majority of COVID-19 now being acquired through community spread, prevention of COVID-19 complications in pre-hospital cases will be crucial in order to prevent an overwhelming of resources (healthcare and economy), especially when preventative and curative interventions are still under development. Such therapies are important not only in the current global situation but will remain an important asset throughout and after the management of this pandemic.

SUMMARY

In an aspect, there is provided an effective method for treating a person afflicted with COVID-19 or acute respiratory distress syndrome (ARDS). In another aspect, there is provided a formulation for being administered intravenously. In a further aspect, there is provided an effective treatment for acute and disproportionate inflammatory respiratory complications caused by COVID-19 infection presenting in moderate to severe symptomatic patients. These and other aspects are described in various embodiments herein.

An embodiment of the invention comprises a method for reducing complications related to COVID-19 or acute respiratory distress syndrome (ARDS) comprising administering dapsone ($C_{12}H_{12}N_2O_2S$), also known as 4,4'-diaminodiphenyl sulfone, to a person afflicted with COVID-19 or ARDS.

Another embodiment of the invention comprises a method of suppressing an autoimmune reaction to COVID-19 in a person afflicted with COVID-19 comprising administering an effective dosage of dapsone to the person. According to a preferred embodiment, the effective dosage of dapsone is eighty-five milligrams of dapsone administered to the afflicted person twice per day.

Another embodiment of the invention comprises a method of suppressing an autoimmune reaction to COVID-19 in a person afflicted with COVID-19 comprising administering an effective dosage of dapsone to the person for a predetermined period of time. According to an embodiment, the predetermined period of time is ten to twenty-one days. According to a preferred embodiment, the predetermined period of time is ten to fourteen days.

Another embodiment of the invention comprises a method of alleviating symptoms related to COVID-19 comprising administering an effective dosage of dapsone to a person afflicted with COVID-19. The symptoms can comprise fever, chills, cough, shortness of breath, difficulty breathing, muscle aches, headache, loss of taste, loss of smell, sore throat, congestion, runny nose, nausea, vomiting, diarrhea, fatigue, difficulty waking up, and/or difficulty staying awake.

Another embodiment of the invention comprises a method of treating a person afflicted with COVID-19 comprising administering to the person a dosage of dapsone. According to an embodiment of the invention, the dosage of dapsone is 75-100 milligrams (mg) of dapsone to the person twice per day.

Another embodiment of the invention comprises a method of treating a person afflicted with COVID-19 comprising administering 80-90 milligrams of dapsone to the person twice per day.

Another embodiment of the invention comprises a method of treating a person afflicted with COVID-19 comprising administering 75-100 milligrams of dapsone to the person twice per day for a predetermined period of time. According to an embodiment of the invention, the predetermined period of time is ten to twenty-one days. According to a preferred embodiment, the predetermined period of time is ten to fourteen days.

Another embodiment of the invention comprises a method of treating a person afflicted with COVID-19 comprising administering 75-100 milligrams of dapsone to the person twice per day for ten days.

Another embodiment of the invention comprises a method of treating a person afflicted with COVID-19 comprising administering 75-100 milligrams of dapsone to the person twice per day for fourteen days.

Another embodiment of the invention comprises a method of treating a person afflicted with COVID-19 comprising administering 75-100 milligrams of dapsone to the person twice per day for twenty-one days.

Another embodiment of the invention comprises a method of treating a person afflicted with COVID-19 comprising administering 80-90 milligrams of dapsone to the person twice per day for ten days.

Another embodiment of the invention comprises a method of treating a person afflicted with COVID-19 comprising administering 80-90 milligrams of dapsone to the person twice per day for fourteen days.

Another embodiment of the invention comprises a method of treating a person afflicted with COVID-19 comprising administering 80-90 milligrams of dapsone to the person twice per day for twenty-one days.

Another preferred embodiment of the invention comprises a method of treating a person afflicted with COVID-19 comprising administering 85 milligrams of dapsone to the person twice per day for ten days.

Another preferred embodiment of the invention comprises a method of treating a person afflicted with COVID-19 comprising administering 85 milligrams of dapsone to the person twice per day for fourteen days.

Another embodiment of the invention comprises a method of treating a person afflicted with COVID-19 comprising administering 85 milligrams of dapsone to the person twice per day for twenty-one days.

Another embodiment of the invention comprises a method of treating a person afflicted with COVID-19 comprising providing a dosage of dapsone in micronized powder form, and providing an inhaler apparatus adapted to dispense micronized powder. The inhaler is supplied with the dosage of dapsone, and the afflicted person is administered the dosage of dapsone via the inhaler. According to an embodiment of the invention, the dosage of dapsone can be 75-100 milligrams of dapsone.

Another embodiment of the invention comprises a method of treating a person afflicted with COVID-19 comprising providing an inhaler apparatus comprising a liquid solution comprising 75-100 milligrams of dapsone, and administering the dosage of dapsone to the person via the inhaler.

Another embodiment of the invention comprises a method of treating a person afflicted with COVID-19 comprising providing an inhaler apparatus supplied with a formulation comprising dapsone and at least one antibiotic, such as azithromycin and/or doxycycline. The formulation is administered to the afflicted person via the inhaler.

Another embodiment of the invention comprises a solution comprising dapsone adapted for nasal delivery.

Another embodiment of the invention comprises a suspension comprising dapsone adapted for nasal delivery.

Another embodiment of the invention comprises a nasal spray comprising dapsone in an aqueous solution. According to another embodiment of the invention, a nasal spray comprises dapsone in a solution comprising a mixture of liquid solvents. Yet another embodiment of the invention comprises a nasal suspension comprising dapsone.

Another embodiment of the invention comprises a method of treating a person afflicted with COVID-19 by administering into the person's nasal cavity about fifty milliliters of a liquid solution comprising 5-200 milligrams of dapsone.

Another embodiment of the invention comprises a nasal spray comprising 5-200 milligrams of dapsone in a fifty milliliter liquid solution.

Another embodiment of the invention comprises a method of treating a person afflicted with COVID-19 by dispensing into the person's nasal cavity a nasal spray comprising dapsone, glycerin, and at least one co-emulsifier selected from the group consisting of lauroyl polyoxyl-6 glycerides and oleoyl polyoxyl-6 glycerides.

Another embodiment of the invention comprises a nasal spray comprising dapsone, glycerin, and at least one co-emulsifier selected from the group consisting of lauroyl polyoxyl-6 glycerides and oleoyl polyoxyl-6 glycerides. According to an embodiment of the invention, the nasal spray can further comprise absolute alcohol. According to another embodiment, the nasal spray further comprises water. According to another embodiment of the invention, the nasal spray also includes at least one antibiotic, such as azithromycin and/or doxycycline.

Another embodiment of the invention comprises a nasal spray comprising dapsone and azithromycin.

Another embodiment of the invention comprises a nasal spray comprising dapsone and doxycycline.

Another embodiment of the invention comprises a nasal spray comprising dapsone, azithromycin and doxycycline.

Another embodiment of the invention comprises a method of treating a person afflicted with COVID-19 by administering into the person's nasal cavity a nasal gel comprising dapsone, castor oil and at least one co-emulsifier selected from the group consisting of lauroyl polyoxyl-6 glycerides and oleoyl polyoxyl-6 glycerides.

Another embodiment of the invention comprises a nasal gel comprising dapsone, castor oil and at least one co-emulsifier selected from the group consisting of lauroyl polyoxyl-6 glycerides and oleoyl polyoxyl-6 glycerides. According to another embodiment of the invention, the nasal gel further includes absolute alcohol, propylene glycol, silicon dioxide, polyacrylic acid and/or water.

Another embodiment of the invention comprises nasal drops comprised of a solution comprising dapsone. Another embodiment of the invention comprises nasal drops comprised of a suspension comprising dapsone.

Another embodiment of the invention comprises a formulation adapted for nasal delivery comprising dapsone and a non-replicating delivery system. The formulation can comprise a micro-emulsion comprising dapsone nanoparticles and a muco-adhesive agent, such as polycarbophil.

Another embodiment of the invention comprises a method of treating a person afflicted with COVID-19 by administering into the person's ear an otic formulation comprising dapsone, and at least one co-emulsifier, such as lauroyl polyoxyl-6 glycerides and/or oleoyl polyoxyl-6 glycerides.

Another embodiment of the invention comprises an otic formulation comprising dapsone and at least one co-emulsifier, such as lauroyl polyoxyl-6 glycerides and/or oleoyl polyoxyl-6 glycerides. According to an embodiment, the formulation further comprises isopropyl alcohol, isopropyl myristate and/or light mineral oil.

Another embodiment of the invention comprises a method of treating a person afflicted with COVID-19 by administering a solution comprising dapsone orally to the afflicted person.

Another embodiment of the invention comprises an oral solution comprising dapsone, alcohol, propylene glycol, and glycerin.

Another embodiment of the invention comprises an oral suspension comprising dapsone.

Another embodiment of the invention comprises a patch comprising dapsone. The patch is adapted to be placed on the skin of the patient, and the dapsone is absorbed through the patient's skin.

Another embodiment of the invention comprises a slow release patch comprising dapsone, absolute alcohol, propylene glycol, cetostearyl alcohol, and at least one co-emulsifier, such as lauroyl polyoxyl-6 glycerides and/or oleoyl polyoxyl-6 glycerides.

Another embodiment of the invention comprises a fast release patch comprising dapsone, absolute alcohol, propylene glycol, cetostearyl alcohol, diethylene glycol monoethyl ether (also known as TRANSCUTOL), and at least one co-emulsifier, such as lauroyl polyoxyl-6 glycerides and/or oleoyl polyoxyl-6 glycerides.

Another embodiment of the invention comprises a method of treating a person afflicted with an inflammatory bowel disease comprising providing a suppository comprising dapsone and positioning the suppository in the afflicted person's rectum.

Another embodiment of the invention comprises a suppository comprising dapsone.

Another embodiment of the invention comprises a method of treating a person afflicted with acute respiratory distress syndrome in which the afflicted person is administered a dosage of dapsone. According to an embodiment of the invention, the dosage of dapsone can be 75-100 milligrams of dapsone given twice per day.

Another embodiment of the invention comprises a method of treating a person afflicted with acute respiratory distress syndrome in which the afflicted person is administered a dosage of 80-90 milligrams of dapsone twice per day.

Another embodiment of the invention comprises a method of treating a person afflicted with acute respiratory distress syndrome in which the afflicted person is administered a dosage of eighty-five milligrams of dapsone to the person twice per day.

Another embodiment of the invention comprises a method of treating a person afflicted with acute respiratory distress syndrome comprising administering 75-100 milligrams of dapsone to the person twice per day for ten to twenty-one days.

Another embodiment of the invention comprises a method of treating a person afflicted with acute respiratory distress syndrome comprising administering eighty-five milligrams of dapsone to the afflicted person twice per day for ten days.

Another embodiment of the invention comprises a formulation adapted for nasal inhalation comprising dapsone and at least one antibiotic selected from the group consisting of azithromycin and doxycycline.

Another embodiment of the invention comprises a formulation comprising 5 to 200 milligrams of dapsone, 50 to 2000 milligrams of azithromycin, 25 to 200 milligrams of doxycycline.

According to an embodiment of the invention, a method for treating a person afflicted with COVID-19 or ARDS comprises administering to the afflicted person a dosage of 75-100 milligrams (mg) of dapsone ($C_{12}H_{12}N_2O_2S$) twice per day.

According to an embodiment of the invention, a method for treating a person afflicted with COVID-19 or ARDS comprises administering to a person afflicted with COVID-19 or ARDS a dosage of 75-100 milligrams (mg) of dapsone twice per day for ten to twenty-one days.

According to a preferred embodiment of the invention, a method for treating a person afflicted with COVID-19 or ARDS comprises administering to the afflicted person a dosage of 80-90 milligrams (mg) of dapsone twice per day for ten days.

According to another preferred embodiment of the invention, a method for treating a person afflicted with COVID-19 or ARDS comprises administering to the afflicted person a dosage of 80-90 milligrams (mg) of dapsone twice per day for fourteen days.

According to another preferred embodiment of the invention, a method of treating a person afflicted with COVID-19 or ARDS comprises administering to the afflicted person eighty-five milligrams (mg) of dapsone twice per day for ten days.

According to another preferred embodiment of the invention, a method of treating a person afflicted with COVID-19 or ARDS comprises administering to the afflicted person eighty-five milligrams (mg) of dapsone twice per day for fourteen days.

Another embodiment of the invention comprises a formulation adapted to be administered intravenously to a person afflicted with COVID-19 or ARDS. The formulation comprises dapsone and a mixture of diluents. According to a preferred embodiment of the invention, the diluents can comprise alcohol, PEG-60 hydrogenated castor oil, polysorbate 80, and water.

Another embodiment of the invention comprises a kit comprised of a first container containing dapsone and a second container containing diluents. The diluents can comprise alcohol, PEG-60 hydrogenated castor oil, polysorbate 80, and water.

Another embodiment of the invention comprises a method of treating a person afflicted with pneumonia by administering a formulation comprised of dapsone and at least one antibiotic, such as azithromycin and/or doxycycline. The formulation can be administered using an inhaler.

Another embodiment of the invention comprises a method of treating a person afflicted with bronchitis by administering a formulation comprised of dapsone and at least one antibiotic, such as azithromycin and/or doxycycline. The formulation can be administered to the afflicted person using an inhaler.

Another embodiment of the invention comprises a method of treating a person afflicted with pneumonia or bronchitis comprising using an inhaler to administer to the afflicted person a formulation comprised of dapsone and azithromycin.

Another embodiment of the invention comprises a method of treating a person afflicted with pneumonia or bronchitis comprising using an inhaler to administer to the afflicted person a formulation comprised of dapsone and doxycycline.

Another embodiment of the invention comprises a method of treating a person afflicted with pneumonia or bronchitis comprising using an inhaler to administer to the afflicted person a formulation comprised of dapsone, azithromycin and doxycycline.

Another embodiment of the invention comprises a pharmaceutical formulation to be administered via nasal inhalation comprising micronized particles of dapsone. The micronized particles have a diameter of one to five micrometers, and eighty percent of the micronized particles have a diameter of two to four micrometers. According to an embodiment, the pharmaceutical formulation includes a propellant, such as hydrofluoroalkane or a chlorofluorocarbon. According to another embodiment, the formulation further comprises lactose monohydrate.

Another embodiment of the invention comprises a method of treating a person afflicted with COVID-19 comprising administering to the person a dosage of dapsone comprising 75-100 milligrams of dapsone twice per day. According to a preferred embodiment of the invention, the dapsone is provided in a dry powder formulation comprising micronized particles of dapsone, and an inhaler apparatus adapted to dispense the dry powder formulation is provided. The inhaler apparatus is suppled with the dry powder formulation, and the dry powder formulation is administered to the person nasally via the inhaler. According to an embodiment, the micronized particles of dapsone have a diameter of one to five micrometers, and eighty percent of the micronized particles have a diameter of two to four micrometers. The dry powder formulation can comprise a propellant, a blending excipient such as lactose monohydrate, and an antibiotic such as azithromycin and doxycycline. According to an embodiment of the invention, the inhaler apparatus can comprise a single dose dry powder inhaler. According to an alternative embodiment, the inhaler apparatus can comprise a multiple dose dry powder inhaler.

DETAILED DESCRIPTION OF PREFERRED EMBODIMENTS

Dapsone, also known as 4,4'-diamino-diphenyl sulfone or DDS, is an aniline derivative belonging to the group of synthetic sulfones. It has dual functions, having both anti-microbial effects and anti-inflammatory features. Dapsone's anti-microbial effects stem from its sulfonamide-like ability to inhibit the synthesis of dihydrofolic acid. It is listed on the World Health Organization's List of Essential Medicines, as one of the safest and most effective medicines needed in a health system (World Health Organization Model List of Essential Medicines, 2019). Processes for the synthesis of dapsone are disclosed in U.S. Pat. Nos. 7,531,694 and 9,845,289, which are incorporated herein by reference.

Dapsone's anti-inflammatory properties stem from inhibition of the production of reactive oxygen species (ROS), reducing the effect of eosinophil peroxidase on mast cells and down-regulating neutrophil-mediated inflammatory responses. More specifically, dapsone inhibits the myeloperoxidase-$H_2O_2$-halide-mediated cytotoxic system in polymorphonucleocytes. As part of the respiratory burst that neutrophils use to kill bacteria, myeloperoxidase converts hydrogen peroxide ($H_2O_2$) into hypochlorous acid (HOCl). HOCl is the most potent oxidant generated by neutrophils and, beyond bactericidal effects, can cause significant host tissue damage during inflammation. Dapsone arrests myeloperoxidase in an inactive intermediate form, reversibly inhibiting the enzyme. This prevents the accumulation of HOCl and reduces tissue damage during inflammation.

Dapsone can suppress intra- and extracellular production of superoxide ($O_2$—) and elastase release triggered by FLMP and physiological agonist C5a, but not by PMA. Both FMLP and C5a signal the above pathways by inducing calcium influx, but PMA functions bypassed calcium influx. Dapsone is capable of antagonizing the induction of calcium influx (FMLP: N-formyl-L-methionyl-L-leucyl-L-phenylalanine, PMA phorbol myristate acetate, PKC protein kinase C, NADPH nicotinamide adenosine dinucleotide phosphate).

Dapsone inhibits IL-8 secretion from human bronchial epithelial cells stimulated with lipopolysaccharide and resolves airway inflammation in the ferret. IL-8 is an important activator cytokine and chemo-attractant for neutrophils that is produced by normal human bronchial epithelial (NHBE) cells through mitogen-activated protein kinase (MAPK) and nuclear factor-κB (NF-κB) p65 pathways. Dapsone has been shown to inhibit the zymosan-mediated human neutrophil respiratory burst and inhibits interleukin-1-stimulated neutrophil adhesion to transformed human umbilical vein endothelial cells. It has been proposed that the anti-inflammatory action of dapsone (e.g., the inhibition of neutrophil adherence—dapsone inhibits beta2 integrin (CD11b/CD18)-mediated adherence of human neutrophils) is associated with inhibition of chemoattractant-induced signal transduction: dapsone interferes with the activation or function of the G-protein (Gi type) that initiates the signal transduction cascade.

Dapsone is considered as an immune-modulatory or immune-suppressive drug, like hydroxyl-chloroquine and colchicine. Dapsone is considered also as a neutrophil migration inhibitor, as reported for colchicine and IL-1 antagonists. Dapsone may be useful in treating neutrophilic airway inflammation and therefore may mitigate the cytokine storm triggered by COVID-19. Dapsone has been used prophylactically in HIV-infected patients and in the treatment of *pneumocystis jirovecii* pneumonia (Australian Medicines Handbook 2006, 2006).

The US Food and Drug Administration (FDA)-approved indications for dapsone are leprosy, dermatitis herpetiformis, and acne vulgaris. It is also a useful adjunct therapeutic agent to many skin disorders. Treatment with dapsone aims to target neutrophil activation and to reduce accumulation of reactive oxygen intermediates during a rapidly evolving and potentially maladaptive immune response.

Dapsone offers many advantages. It presents a scientifically sound mechanism of action and is a relatively affordable generic drug. Dapsone is efficiently absorbed (70%-80%) from the gastrointestinal tract and is therefore amenable to outpatient settings. Dapsone reaches peak serum concentration in 2-6 hours and has a mean half-life of 20-30 hours. Dapsone is adequately distributed to the fluid of the alveolar spaces. Dapsone's metabolic, pharmacokinetic and toxicological profiles are well documented.

Neutrophil influx into the extravascular compartments of the lungs is a defining characteristic of Acute Respiratory Distress Syndrome (ARDS). This has been reported regardless of the initial event triggering ARDS, has been associated with COVID-19 and earlier reported in association with SARS-CoV. Interleukin IL-8 is an important activator cytokine and chemo-attractant for neutrophils produced by normal human bronchial epithelial cells. Dapsone inhibits IL-8 secretion from human bronchial epithelial cells stimulated with lipopolysaccharide and in animal studies has shown to resolves airway inflammation. In neutrophilic dermatological conditions, dapsone's effectiveness has been largely through the inhibition of IL-8 mediated neutrophil chemotaxis leading to favorable outcomes even without interfering with the underlying pathology. Dapsone has the potential to alleviate the pulmonary inflammatory phase triggered by COVID-19 and prevent the hospitalization of many patients afflicted with COVID-19 around the world.

It is believed that the addition of dapsone to standard of care in symptomatic SARS-CoV-2 positive patients may be more effective in reducing COVID-19 complications requiring hospitalization with or without intensive care unit admission, and further complications such as intubation with invasive mechanical ventilation support, and mortality when compared to standard care alone.

An embodiment of the invention comprises a method of treating patients with COVID-19 comprising the use of dapsone (4,4'-diaminodiphenylsulfone) in an early treatment approach to arrest COVID-19 complications. According to a preferred embodiment of the invention, a person afflicted with COVID-19 is given a dosage of 80-90 milligrams (mg) of dapsone twice per day. It is be believed that this can suppress an autoimmune reaction to COVID-19 in the person afflicted with COVID-19, and alleviate COVID-19 symptoms, such as fever, chills, cough, shortness of breath, difficulty breathing, muscle aches, headache, loss of taste, loss of smell, sore throat, congestion, runny nose, nausea, vomiting, diarrhea, fatigue, difficulty waking up, and/or difficulty staying awake.

According to an embodiment, the afflicted patient is given 85 mg of dapsone twice daily for a period of ten to twenty-one days. The dosage of dapsone can be administered to the patient in tablet form. According to another embodiment of the invention, an extended release tablet containing 160-180 mg of dapsone is administered once daily for a period of ten to twenty-one days.

Preferably, the afflicted patient is administered 85 mg of dapsone twice daily for ten days. In another preferred embodiment, the afflicted patient is given 85 mg of dapsone twice daily for fourteen days.

According to an embodiment of the invention, a patient is given 80-90 mg of dapsone twice daily or an extended release tablet of 160-180 mg of dapsone once per day for COVID-19 or ARDS prevention upon patient diagnosis before respiratory distress.

Another embodiment of the invention comprises a dapsone formulation for intravenous delivery. The formulation comprises dapsone and a mixture of diluents. The diluents can be comprised of alcohol, PEG-60 hydrogenated castor oil, polysorbate 80, and water (as needed). Preferably, the alcohol is absolute alcohol (ethanol containing no more than one percent water). Preferred embodiments of the intravenous formulation are shown in the following table. (The concentration of each of the ingredients can be varied by ±30%.)

Intravenous Formulation

| Ingredient (mg) | Containers | Concentrations (mg dapsone per mL of Containers A and B formulation) | | | | |
| --- | --- | --- | --- | --- | --- | --- |
| | | 5 mg dapsone/ mL | 25 mg dapsone/ mL | 85 mg dapsone/ mL | 100 mg dapsone/ mL | 200 mg dapsone/ mL |
| Dapsone | Container A (Drug) | 5 mg | 25 mg | 85 mg | 100 mg | 200 mg |
| Absolute Alcohol | Container B (Diluent) | 32.9% | 32.9% | 32.9% | 32.9% | 32.9% |
| PEG-G0 Hydrogenated Castor Oil | | 65% | 65% | 65% | 65% | 65% |
| Glycerine | | 15% | 15% | 15% | 15% | 15% |
| Polysorbate 80 | | 20% | 20% | 20% | 20% | 20% |

-continued

| Ingredient (mg) | Containers | Concentrations (mg dapsone per mL of Containers A and B formulation) | | | | |
|---|---|---|---|---|---|---|
| | | 5 mg dapsone/ mL | 25 mg dapsone/ mL | 85 mg dapsone/ mL | 100 mg dapsone/ mL | 200 mg dapsone/ mL |
| Water for injection/ 0.9% Sodium Chloride Injection or 5% Dextrose | | qs | qs | qs | qs | qs |

According to a preferred embodiment, the formulation is supplied in two separate containers. Container A will have dapsone drug substance that is sterile and will receive sterile solvent mixture from container B (children 5 mg/Kg BW, 25 mg, 85 mg and 200 mg adult dose). Container B contains a mixture of diluent as listed in the above table. Preferably, there is a total of 20-100 milliliters (mL) of diluent mixture contained in container B. The diluent mixture is drawn from container B with a sterile syringe and added to container A. The contents of container A are mixed, and the required dose is injected into an IN drip bag. The IN drip bag is administered to the patient.

An embodiment of the invention comprises a method for treating a hospitalized patient using an incremental dosage of dapsone over four days at hospitalization due to ARDS (cytokine storm rescuer). The dosage can be administered by intramuscular injection (IM), subcutaneously, or intravenously. For IM or subcutaneous delivery when the patient is hospitalized under the effect of a cytokine storm, the dosage can be 150 mg twice daily (bid) the first day, 300 mg bid the second day, and 600 mg bid the third and fourth days. For intravenous delivery, the dosage can be 75 mg bid the first day, 150 mg bid the second day, and 300 mg bid on the third and fourth days.

According to another embodiment of the invention, dapsone can be administered nasally. Nasal drug delivery can be helpful where oral ingestion of dapsone (tablets/solutions/suspensions) is difficult. Rapid adsorption via nasal presentation of dapsone spray/gel/drops is effective due to abundant capillary vessels, fast onset of action, avoidance of hepatic first-pass metabolism, utility for chronic medication and ease of administration, especially in children and geriatric populations. Additionally, nasal presentation will avoid first portal circulation, thereby maximizing beneficial effects of the drug for a longer time compared to oral route.

The nasal spray and nasal gel versions are lipid based and help increase residence time of the drug in the nasal mucosal lining for a longer time and, thus, increasing maximal absorption of presented drug. Additionally, nasal presentation avoids first portal circulation, thereby maximizing beneficial effects of the drug for a longer time compared to oral route. It is believed that some dapsone active from the spray and gel applied to the nasal membranes will also go directly to lungs lining, thereby, providing relief much faster than the oral ingestion route. Benefits of presentation via nasal drops is similar to nasal gel. Additionally, drops will benefit both pediatric and geriatric patients who are unable to take tablets.

An embodiment of the invention comprises a nasal spray comprising dapsone in a solution or suspension. According to an embodiment of the invention, a nasal spray comprises dapsone in an aqueous solution. According to yet another embodiment of the invention, a nasal spray comprises dapsone in a solution comprising a mixture of liquid solvents. Preferably, the nasal spray comprises particles having a diameter of ten micrometers (μm).

A preferred embodiment of the invention comprises a nasal spray comprised of dapsone, LABRAFIL M1944CS (oleoyl polyoxyl-6 glycerides), absolute alcohol, glycerine ($C_3H_8O_3$), and liquid water ($H_2O$) as needed. Preferred formulations of the nasal spray are shown in the table below. (The concentration of each ingredient can be varied by ±30%.)

Nasal Spray

| Ingredient | Concentrations (mg dapsone per 50 mL of nasal spray) | | | |
|---|---|---|---|---|
| | 5 mg | 25 mg | 85 mg | 200 mg |
| Dapsone | 5 mg | 25 mg | 85 mg | 200 mg |
| LABRAFIL M1944CS | 25 mL | 25 mL | 25 mL | 25 mL |
| Absolute Alcohol | 0.5 mL | 0.5 mL | 0.5 mL | 0.5 mL |
| Glycerine | 4.5 mL | 4.5 mL | 4.5 | 4.5 mL |
| Aqua (Water) | qs | qs | qs | qs |

An embodiment of the invention comprises a method of treating a person afflicted with COVID-19 by administering to the afflicted person a nasal spray comprising dapsone. The nasal spray can be one of the nasal spray formulations described above. Another embodiment of the invention comprises a method of treating a person afflicted with ARDS by administering any one of the nasal spray formulations described above. Any one of the nasal spray formulations described above can also be used in methods for treating seasonal or perennial rhinitis, nasal polyposis and/or infectious sinusitis. According to another embodiment of the invention, the nasal spray also includes at least one antibiotic, such as azithromycin and/or doxycycline.

Another embodiment of the invention comprises a nasal gel comprising dapsone. The nasal gel can be comprised of dapsone, LABRAFIL M2130CS (Lauroyl polyoxyl-6 glycerides), LABRAFIL M1944CS (oleoyl polyoxyl-6 glycerides), absolute alcohol, propylene glycol, castor oil, silicon dioxide, Carbomer 934P (polyacrylic acid), and water as needed. Preferred formulations of the nasal gel are shown in the table below. (The concentration of each of the ingredients can be varied by ±30%.)

Nasal Gel

| | Concentrations (mg dapsone per 100 mL of nasal gel) | | | |
|---|---|---|---|---|
| Ingredient | 5 mg | 25 mg | 85 mg | 200 mg |
| Dapsone | 5 mg | 25 mg | 85 mg | 200 mg |
| LABRAFIL M2130CS | 5 mL | 5 mL | 5 mL | 5 mL |
| LABRAFIL M1944CS | 40 mL | 40 mL | 40 mL | 40 mL |
| Absolute Alcohol | 0.5 mL | 0.5 mL | 0.5 mL | 0.5 mL |
| Propylene Glycol | 5 mL | 5 mL | 5 mL | 5 mL |
| Castor Oil | 40 mL | 40 mL | 40 mL | 40 mL |
| Silicon Dioxide | 0.5 mL | 0.5 mL | 0.5 mL | 0.5 mL |
| Carbomer 934P | 0.5 mL | 0.5 mL | 0.5 mL | 0.5 mL |
| Aqua | qs | qs | qs | qs |

Another embodiment of the invention comprises nasal drops comprising dapsone. Preferred formulations of the nasal drops are provided in the table below. (The concentration of each of the ingredients can be varied by ±30%.)

Nasal Drops

| | Concentrations (mg dapsone per 50 mL of nasal drop) | | | |
|---|---|---|---|---|
| Ingredient | 5 mg | 25 mg | 85 mg | 200 mg |
| Dapsone | 5 mg | 25 mg | 85 mg | 200 mg |
| LABRAFIL M2130CS | 5 mL | 5 mg | 5 mg | 5 mL |
| LABRAFIL M1944CS | 40 mL | 40 mg | 40 mL | 40 mL |
| Absolute Alcohol | 0.5 mL | 0.5 mg | 0.5 mL | 0.5 mL |
| Glycerine | 4.5 mL | 4.5 mg | 4.5 mL | 4.5 mL |

The nasal spray and nasal gel embodiments are lipid based and help increase residence time of the drug in the nasal mucosal lining, thus increasing maximal absorption of presented drug. These modes are particularly beneficial for treatment of allergic, inflammatory, or infectious sinusitis. In the spray and gel embodiments, it is believed that some dapsone active from the spray and gel applied to the nasal membranes goes directly to the lining of the lungs, thereby providing relief much faster than the oral ingestion route. Benefits of nasal drops presentation are similar to nasal gel. Additionally, nasal drops benefit both pediatric and geriatric patients who are unable to take tablets.

Another embodiment of the invention comprises a slow release intranasal formulation comprising dapsone and a non-replicating delivery system. The formulation can be used in a nasal spray and/or nasal drops. The formulation comprises a micro-emulsion comprising dapsone nanoparticles, a muco-adhesive agent, such as polycarbophil, and a polymeric microemulsion drug delivery system. The muco-adhesive agent binds to the mucous membrane of the nasal passage to provide a long-term slow release of dapsone nanoparticles to the mucosal linings of the nasal passage. The dapsone nanoparticles preferably have a diameter of 5 to 45 micrometers (μm). The microemulsion drug delivery system can be comprised of LABRAFIL M2130CS, a solubilizer/emulsifying agent such as CREMOPHORE RH 40 (polyoxyl 40 hydrogenated castor oil), and a solvent/carrier such as TRANSCUTOL CG (ethoxydiglycol). Preferred formulations of the slow release intranasal formulation are provided in the table below. (The concentration of each of the ingredients can be varied by ±30%.)

Slow Release Intranasal Formulation

| | Concentrations (mg dapsone per 50 mL of nasal formulation) | | | |
|---|---|---|---|---|
| Ingredient | 5 mg | 25 mg | 85 mg | 200 mg |
| Dapsone (nanoparticles 5 to 45 μm) | 5 mg | 25 mg | 85 mg | 200 mg |
| Polymer containing microemulsion drug delivery system (LABRAFIL M2130CS + CREMOPHOR RH 40 + TRANSCUTOL CG) | 30% | 30% | 30% | 30% |
| Polycarbophil | 4% | 4% | 4% | 4% |
| Water | qs (50-65%) | qs (50-65%) | qs (50-65%) | qs (50-65%) |

Another embodiment of the invention comprises an otic formulation comprising dapsone. Otic formulations are helpful for ear-related infections for patients of various ages, as well as for otitis media. Dapsone has strong antimicrobial as well as anti-inflammatory properties. It is believed that this presentation can relieve patients of ear infections as well as the inflammatory responses, thus alleviating discomfort and pain. Preferred otic formulations are provided in the table below. (The concentration of each ingredient can be varied by ±30%.)

Otic Formulations

| | Concentrations (mg dapsone per 50 mL) | | |
|---|---|---|---|
| Ingredient | 25 mg | 85 mg | 200 mg |
| Dapsone | 5 mg | 85 mg | 200 mg |
| LABRAFIL M2130CS | 25 mL | 25 | 5 |
| LABRAFIL M1944CS | 20 mL | 20 | 25 |
| Isopropyl Alcohol | 0.5 mL | 0.5 | 20 |
| Isopropyl Myristate ($C_{17}H_{34}O_2$) | 0.024 mL | 0.024 | 0.024 |
| Light Mineral Oil | qs | qs | qs |

Embodiments of the invention include oral solutions and suspensions. Oral solutions and suspensions can be beneficial to patients, which have difficulty swallowing tablets, especially in pediatric and geriatric populations. Solution presentation can be easy to administer to children either by a syringe or a spoon/dosing cup.

Another embodiment of the invention comprises an oral solution comprising dapsone. An oral solution according to an embodiment of the invention can be comprised of dapsone, absolute alcohol, propylene glycol, and glycerin. Preferred embodiments of the oral solution are provided in the table below. (The concentration of each ingredient can be varied by ±30%.)

Oral Solution

|  | Concentrations/100 mL | | | |
| --- | --- | --- | --- | --- |
| Ingredient | 5 mg | 25 mg | 85 mg | 200 mg |
| Dapsone | 5 mg | 25 mg | 85 mg | 200 mg |
| Absolute Alcohol | 25 mL | 30 mb | 40 mL | 10 mL |
| Propylene Glycol | 30 mL | 30 mL | 30 mL | 90 mL |
| Glycerin | 10 mL | 10 mL | 10 mL | 15 mL |
| Sweetener (Sucralose/Stevia) | 10 g | 10 g | 10 g | 10 g |
| Flavor | 0.2 g | 0.2 g | 0.2 g | 0.2 g |
| Medium-chain Triglycerides (MCT) Oil | qs | qs | qs | qs |

Another embodiment of the invention comprises an oral suspension comprising dapsone. Oral suspension is of greater use in both pediatric and geriatric patents who have difficulty swallowing. A more viscous suspension as well as a thicker solution will not cause any swallowing related aspiration pneumonia in patients. Also, a thicker solution/suspension taken orally is easier to swallow, especially in elderly patients with stroke, ALS or Parkinson's diseases. Preferred embodiments of the oral suspension are shown in the table below. (The concentration of each ingredient can be varied by ±30%.)

Oral Suspension

|  | Concentrations/100 mL | | | |
| --- | --- | --- | --- | --- |
| Ingredient | 5 mg | 25 mg | 85 mg | 200 mg |
| Dapsone | 5 mg | 25 mg | 85 mg | 200 mg |
| Propylene Glycol | 40 mL | 50 mL | 60 mL | 70 mL |
| Carbomer 934P (Carbopol ® 974P), NF | 4.5 g | 4.5 g | 4.5 g | 4.5 g |
| Glycerin | 0 mL | 10 mL | 10 mL | 10 mL |
| Potassium sorbate | 0.2 g | 0.2 g | 0.2 g | 0.2 g |
| Poloxamer 188, NF (Polyethylene-polypropylene glycol) | 0.2 g | 0.2 g | 0.2 g | 0.2 g |
| Stevia ($C_{38}H_{60}O_{18}$) Liquid Concentrate | 1.0 mL | 1.0 mL | 1.0 mL | 1.0 mL |
| Flavor | 0.2 mL | 0.2 mL | 0.2 mL | 0.2 mL |
| Purified Water, USP | qs | qs | qs | qs |
| SodiumHydroxide, NF | 0.5 g | 0.5 g | 0.5 g | 0.5 g |

*pH about 5

Another embodiment of the invention comprises a slow release patch comprising dapsone. The slow release patch preferably comprises dapsone, absolute alcohol, propylene glycol, cetostearyl alcohol, and at least one co-emulsifier, such as lauroyl polyoxyl-6 glycerides (LABRAFIL M2130CS) and/or oleoyl polyoxyl-6 glycerides (LABRAFIL M1944CS). Preferred embodiments of the slow release patch are provided in the table below. (The concentration of each ingredient can be varied by ±30%.)

Slow Release Patch

|  | Quantity % (w/w) | | |
| --- | --- | --- | --- |
| Ingredient | 25 mg | 85 mg | 200 mg |
| Dapsone | 25 mg (0.25%) | 85 mg (0.85%) | 200 mg (2%) |
| Absolute Alcohol | 15 | 15 | 15 |
| Propylene Glycol | 15 | 15 | 15 |
| Cetostearyl Alcohol | 5 | 5 | 5 |
| LABRAFIL M2130CS | 10 | 10 | 10 |
| LABRAFIL M1944CS | 40 | 50 | 60 |
| Aqua | qs | qs | qs |

Another embodiment of the invention comprises a fast release patch comprising dapsone. Another embodiment of the invention comprises a fast release patch comprising dapsone, absolute alcohol, propylene glycol, cetostearyl alcohol, diethylene glycal monoethyl ether (also known as TRANSCUTOL), and at least one co-emulsifier, such as lauroyl polyoxyl-6 glycerides (LABRAFIL M2130CS) and/or oleoyl polyoxyl-6 glycerides (LABRAFIL M1944CS). Preferred embodiments of the fast release patch are provided in the table below. (The concentration of each ingredient can be varied by ±30%.)

Fast Release Patch

|  | Quantity % (w/w) | | |
| --- | --- | --- | --- |
| Ingredient | 25 mg | 85 mg | 200 mg |
| Dapsone | 25 mg (0.25%) | 85 mg (0.85%) | 200 mg (2%) |
| Absolute Alcohol | 5 | 10 | 15 |
| Propylene Glycol | 15 | 15 | 15 |
| Cetostearyl Alcohol | 5 | 5 | 5 |
| Transcutol | 10 | 10 | 10 |
| LABRAFIL M2130CS | 10 | 10 | 5 |
| LABRAFIL M1944CS | 30 | 40 | 40 |
| Aqua | qs | qs | qs |

Another embodiment of the invention comprises a dapsone suppository for treatment of inflammatory bowel diseases, such as Crohn's and ulcerating colitis. Preferred embodiments of the suppository are provided in the table below. (The concentration of each ingredient can be varied by ±30%.)

Suppositories

|  | Concentrations (mg dapsone per 2 gram suppository) | | |
| --- | --- | --- | --- |
| Ingredient | 25 mg | 85 mg | 200 mg |
| Dapsone | 25 mg | 85 mg | 200 mg |
| Absolute Alcohol (solvent) | 20 mL | 40 mL | 80 mL |
| Witepsol H 35/ PEG 2000-6000/ Glycerinated gelatin base | 1930 mg | 1800 mg | 1700 mg |
| Light Mineral oil | qs | qs | qs |

Inhalers

Another embodiment of the invention comprises a method of treating a patient afflicted with COVID-19 or ARDS comprising the steps of forming dapsone in a micronized powder form and administering the micronized powder to the patient using an inhaler. The step of forming dapsone into a micronized powder can be accomplished using a thin film freezing process disclosed in U.S. Pat. No. 10,285,945, which is incorporated by reference herein.

An embodiment of the invention comprises an inhaler apparatus that dispenses micronized powder particles of dapsone. The apparatus can comprise an inhaler adapted to deliver a medication in a solid micronized powder form, such as the inhaler disclosed in U.S. Pat. No. 5,207,217, which is incorporated by reference herein. The inhaler can be supplied with a dosage of approximately 75-100 milligrams of dapsone in micronized powder form, and the dosage can be administered to a patient. The inhaler apparatus can be a single dose dry powder inhaler or a multiple dose dry powder inhaler. The inhaler apparatus can be used to treat all viral or bacterial infections that can provoke a cytokine storm. According to another embodiment of the invention, the inhaler is supplied with dapsone and at least one antibiotic, such as azithromycin and/or doxycycline, that can be formed into a dry micronized powder, blended together, and dispensed by the inhaler.

Another embodiment of the invention comprises an inhaler apparatus that dispenses a liquid solution comprising dapsone. The inhaler can dispense a dosage of liquid solution comprising approximately 75-100 milligrams of dapsone. Another embodiment comprises a method of treating respiratory conditions, such as COVID-19, ARDS, chronic obstructive pulmonary disease (COPD), and allergic bronchitis (asthma) comprising administering a liquid solution comprising 75-100 milligrams of dapsone.

Another embodiment of the invention comprises a method of treating pneumonia and/or bronchitis with a formulation comprising dapsone and at least one antibiotic. The antibiotic can be azithromycin and/or doxycycline. The formulation can be administered using an inhaler.

Nasal Inhalation Products

An embodiment of the invention comprises a formulation adapted for nasal inhalation comprising micronized particles of dapsone. The dapsone particles have a diameter in a range of one to five micrometers (μm), with 80% of the particles having an average diameter of 2-4 μm, which facilitates rapid delivery of an effective dosage of dapsone to the disease site. The dapsone particles can be dissolved or suspended into an aerosol propellant, such as a chlorofluorocarbon (CFC), to facilitate movement of the dapsone out of an inhaler. As such, a patient can inhale the dapsone directly into his/her lungs. According to an embodiment of the invention, the formulation is administered to the patient using an inhaler. In a method of treating COVID-19, an amount of the formulation is administered to provide 85 milligrams of dapsone twice per day for twenty-one days.

The formulation can further include a blending excipient. Preferably, the blending excipient is lactose monohydrate. The lactose monohydrate provides an additional wet surface for rapid adherence of micronized dapsone particles on the cellular surface of the lungs, and speeds up the process of absorption and reducing inflammation. The active ingredient can be dissolved or suspended into a propellant, such as a chlorofluorocarbon, to facilitate inhalation directly into the lungs.

In the treatment of patients afflicted with COVID-19 or ARDS, the lung is an attractive target for drug delivery as this tissue is the primary organ that is affected by COVID-19 and ARDS. The cytokine storm and the acute and chronic neutrophilic responses cause pulmonary distress and extreme breathing issues resulting in the use of ventilators on the affected patient. The use of inhalers provides direct access of dapsone to the affected lungs for the treatment of acute and chronic respiratory diseases. This drug presentation uses the large surface area of the lung area, which has a relatively low enzymatic, controlled environment for systemic absorption of medications. In a method of treating COVID-19 and/or ARDS according to an embodiment, the appropriate amount of dapsone is deposited past the oropharyngeal region of the lungs of the patient to achieve therapeutic effectiveness. This delivery of dapsone produces minimal side effects.

Another embodiment of the invention comprises a formulation comprising dapsone and at least one antibiotic, such as azithromycin or doxycycline. An embodiment of the invention comprises a formulation adapted for nasal inhalation comprising a dry powder blend of dapsone and the antibiotic(s). The powder blend can be comprised of dapsone (5 mg to 200 mg), azithromycin (50 mg to 2000 mg), and doxycycline (25 mg to 200 mg). The dry powder blend is mixed with appropriate blending excipients to stabilize the formulation and help in delivery of the dapsone, azithromycin and doxycycline. The formulation can be appropriately blended to deliver from twenty microliters (μL) to 100 μL doses, preferably 25 μL doses. The formulation can further include a blending excipient, such as lactose monohydrate. The formulation can be dissolved or suspended in a propellant such as hydrofluoroalkane (HFA), and packaged in anodized/coated aluminum containers. The active pharmaceutical ingredient (API) is preferably micronized into particles having a diameter in a range from one to five micrometers (μm), with 80% of the particles having an average diameter of 2-4 μm. The blending materials can also be micronized accordingly to generate a homogenous blend of active ingredients and excipients enabling an accurate delivery of the inhaled drum product and rapid absorption by the alveoli in the lungs.

Enemas

Dapsone formulations can also be administered via an enema in a concentration of between 200 mg and 1000 mg. This approach is beneficial when the lesion is located in the upper part of the intestine.

Other Soft Tissue Disorders

COVID-19 is a soft tissue disorder, as it attacks the lining of the alveolar sacs. Other types of soft tissue disorders that can be treated with dapsone include respiratory disorders, including, but not limited to, respiratory infections such as respiratory syncytial virus (RSV) and influenza, chronic obstructive pulmonary disease (COPD) (where dapsone is administered via a nebulizer), chronic lung disease, and cystic fibrosis (particularly early stage to control inflammation). Additionally, graft versus host disease (resulting in a cytokine storm), myositis, such as inflammatory idiopathic myopathies (neutrophilic), rheumatoid arthritis and other collagenous vascular diseases, atherosclerosis, and aging (including telomerase function alteration as an anti-oxidative agent) can be treated by administration of dapsone in a concentration of 75-100 mg twice daily, and preferably 80-95 mg twice daily, and more preferably 80-90 mg twice daily, and still more preferably 85 mg twice daily.

Dapsone formulations and methods of using same are described above. Various changes can be made to the invention without departing from its scope. The above description of embodiments of the invention are provided for the purpose of illustration only and not limitation—the invention being defined by the claims and equivalents thereof.

What is claimed is:

1. A method of treating a person afflicted with acute respiratory distress syndrome comprising administering to the person a dosage of dapsone comprising 75-100 milligrams of dapsone twice per day.

2. The method according to claim 1, wherein the administration is for ten to fourteen days.

3. The method according to claim 1, wherein the dosage of dapsone comprises 80-90 milligrams of dapsone twice per day.

4. The method according to claim 1, wherein the dosage of dapsone comprises eighty-five milligrams of dapsone twice per day.

5. The method according to claim 4, wherein the administration is for is ten days.

6. The method according to claim 1, wherein the administration is for twenty-one days.

7. A method of treating a person afflicted with rhinitis comprising administering a nasal spray into the person's nasal cavity, the nasal spray comprising a dosage of dapsone in a liquid solution, wherein the dosage of dapsone comprises 75-100 milligrams of dapsone and wherein the nasal spray further comprises at least one antibiotic selected from the group consisting of azithromycin and doxycycline.

8. The method according to claim 7, wherein the dosage of dapsone comprises eighty-five milligrams of dapsone.

9. The method according to claim 8, wherein the nasal spray is administered into the person's nasal cavity twice per day.

10. The method according to claim 8, wherein the nasal spray is administered into the person's nasal cavity twice per day for ten to fourteen days.

11. The method according to claim 7, wherein the liquid solution is an aqueous solution.

12. The method according to claim 11, wherein the nasal spray further comprises glycerin, and at least one co-emulsifier selected from the group consisting of lauroyl polyoxyl-6 glycerides and oleoyl polyoxyl-6 glycerides.

13. A method of treating a person afflicted with sinusitis comprising administering a nasal spray into the person's nasal cavity, the nasal spray comprising a dosage of dapsone in a liquid solution, wherein the dosage of dapsone comprises 75-100 milligrams of dapsone and wherein the nasal spray further comprises at least one antibiotic selected from the group consisting of azithromycin and doxycycline.

14. The method according to claim 13, wherein the dosage of dapsone comprises eighty-five milligrams of dapsone.

15. The method according to claim 13, wherein the nasal spray is administered into the person's nasal cavity twice per day for ten to fourteen days.

16. The method according to claim 13, wherein the liquid solution is an aqueous solution, and further wherein the nasal spray further comprises glycerin, absolute alcohol, and at least one co-emulsifier selected from the group consisting of lauroyl polyoxyl-6 glycerides and oleoyl polyoxyl-6 glycerides.

* * * * *